United States Patent
Ching et al.

(10) Patent No.: US 9,220,512 B2
(45) Date of Patent: Dec. 29, 2015

(54) MEDICAL DRILL

(75) Inventors: Jason Shiang Ching, Jhongli (TW); Pei Hua Tsai, Tainan (TW); Jia Bin Li, Jhongli (TW); Hung Cheng Lin, Tainan (TW); Chih Chiang Fu, Kaohsiung (TW)

(73) Assignee: National Central University, Jhongli, Taoyuan County (TW)

( * ) Notice: Subject to any disclaimer, the term of this patent is extended or adjusted under 35 U.S.C. 154(b) by 606 days.

(21) Appl. No.: 13/430,310

(22) Filed: Mar. 26, 2012

(65) Prior Publication Data

US 2012/0265206 A1 Oct. 18, 2012

(30) Foreign Application Priority Data

Apr. 18, 2011 (TW) ............... 100113363 A

(51) Int. Cl.
 *A61B 17/16* (2006.01)
 *A61C 3/02* (2006.01)
 *A61C 1/00* (2006.01)

(52) U.S. Cl.
 CPC . *A61B 17/16* (2013.01); *A61C 1/00* (2013.01); *A61C 3/02* (2013.01)

(58) Field of Classification Search
 CPC ..... A61B 17/16; A61B 17/1615; C22C 45/10
 USPC ...................................... 606/79–85; 148/304
 See application file for complete search history.

(56) References Cited

U.S. PATENT DOCUMENTS

| 26,613 | A | * | 12/1859 | Phelps ................... 408/210 |
| 3,051,205 | A | * | 8/1962 | Kallio ................... 408/210 |
| 5,567,532 | A | * | 10/1996 | Peker et al. .......... 428/457 |
| 5,891,148 | A | * | 4/1999 | Deckner ............... 606/80 |
| 6,312,432 | B1 | * | 11/2001 | Leppelmeier ........ 606/80 |
| 7,267,513 | B2 | | 9/2007 | Wiker et al. |
| 2009/0208902 | A1 | | 8/2009 | Danger et al. |
| 2009/0325118 | A1 | * | 12/2009 | Lewis et al. ......... 433/10 |
| 2010/0178522 | A1 | * | 7/2010 | Mosimann ........... 428/457 |

FOREIGN PATENT DOCUMENTS

TW 201039949 A 11/2010

OTHER PUBLICATIONS

Chu et al., Characteristic studies on the Zr-based metallic glass thin film fabricated by magnetron sputtering process, Jun. 15, 2008, Elsevier, Surface & Coatings Technology 202, pp. 5564-5566.*
Xing et al., Enhanced plastic strain in Zr-based bulk amorphous alloys, Oct. 1, 2001, Physical Review B, vol. 64, 180201(R).*
Qi, Synthesis of Zr-based amorphous alloy with large supercooled region through mechanical alloying, 1998, Gongneng Cailiao, pp. 1257-1258.*

(Continued)

*Primary Examiner* — Zade Coley
(74) *Attorney, Agent, or Firm* — Muncy, Geissler, Olds & Lowe, P.C.

(57) ABSTRACT

A medical drill is disclosed, which is made of amorphous alloy, the amorphous alloy is zirconium amorphous alloy comprising 45 at % or above of zirconium, wherein the tensile strength of the medical drill is 1500-2500 Mpa, and the Vicker's hardness of the medical drill is 400-750. Moreover, a medical drill made of titanium amorphous alloy is also disclosed.

8 Claims, 3 Drawing Sheets

(56) References Cited

OTHER PUBLICATIONS

Liu et al., Deformation behavior, corrosion resistance, and cytotoxicity of N9-free Zr-bassed bulk metallic glasses, Oct. 23, 2007, Journal of Biomedical Materials Research Part A, 160-169.*

Huang et al., Ni-free Zr—Cu—Al—Nb—Pd metallic glasses with different Zr/Cu ratios for biomedical applications, Jun. 12, 2012, Journal of Biomedical Materials Research Part B, vol. 1008, issue 6, pp. 1472-1482.*

* cited by examiner

MEDICAL DRILL

CROSS REFERENCE TO RELATED APPLICATION

This application claims the benefits of the Taiwan Patent Application Serial Number 100113363, filed on Apr. 18, 2011, the subject matter of which is incorporated herein by reference.

BACKGROUND OF THE INVENTION

1. Field of the Invention

The present invention relates to a medical drill, more particularly, to a medical drill made of an amorphous alloy.

2. Description of Related Art

Generally, during medical surgery related to bone repair, such as hip or knee replacement for treating broken bones, dental implants, and debridement, bone drilling is often necessary for implanting bone screws. For example, in treating a broken bone, a drill can be used to perform a bone drilling process and a bone screw is screwed into the bone to fix the broken bone. During the bone drilling surgery, a medical drill is necessary.

Medical drills are widely used in orthopedic or dental treatment. In general fracture surgery, a space with a certain size and depth would be formed in the bone by a medical drill, and then the location of the bone would be fixed through bone implants, such as bone screws and bone plates. In the dental field, dental drills are used in orthodontic treatment or dental implant treatment to form an opening on a gum and then to fix a bracket or a dental implant.

However, the drills used in the orthopedic and dental fields are generally made of martensitic stainless steel with a crystalline structure and an elastic limit less than 0.5%, and thereby the shift of the normal vector of force away from the center axis often causes the breaking of drills, resulting in surgical inconvenience and even medical disputes.

Regarding medical drills, US 2009208902 discloses a dental drill made of plastics. Also, U.S. Pat. No. 6,312,432 suggests a bone drill, but fails to disclose a novel material for medical drills.

As shown in FIG. 1, a medical drill generally has a pillar body, and threads 11 are formed in a certain portion of the pillar body. However, a conventional medical drill is often made of a crystalline metal, such as stainless steel (e.g. martensitic stainless steel), an alloy, ceramic, or plastic material. Therefore, breaking of medical drills often occurs and causes surgical inconvenience.

Hence, it is desirable to develop for medical drills a novel material which has excellent properties of good fracture resistance, enhanced corrosion resistance, high wear resistance, improved toughness and high hardness, and is advantageous to the operation of orthopedic or dental treatment.

SUMMARY OF THE INVENTION

The present invention provides a medical drill made of an amorphous alloy, in which the amorphous alloy is a Zr-based amorphous alloy which contains zirconium metal in 45 at % or more, and the medical drill has a tensile strength of 1500-2500 MPa and a Vickers hardness of 400-750.

The medical drill according to the present invention can be used as a bone drill or a dental drill. Through tests under practical operation, it can be confirmed that the medical drill made of the amorphous alloy according to the present invention has excellent properties of good fracture resistance, enhanced corrosion resistance, high wear resistance, improved toughness and high hardness compared to conventional medical drills made of crystalline alloys. That is, the conventional art cannot achieve the above-mentioned excellent properties.

In the present invention, the amorphous alloys can be applied in medical bone drills and exhibit better properties compared to the alloy materials used in conventional drills. The drill made of the amorphous material according to the present invention has excellent properties equal to surgical knifes, such as good toughness, high hardness and enhanced fracture resistance, and thus can meet the requirements for medical use.

The amorphous alloys of the present invention include Zr-based amorphous alloys and have higher glass transition temperature and activation energy. In addition, silicon, boron, yttrium, palladium or tantalum may be added into the amorphous alloys to enhance the thermal stability and mechanical properties of the amorphous alloys (or to inhibit crystallized nucleation of supercooled metallic liquid).

So far, little research focuses on the application of amorphous materials in clinical medicine. The Zr-based or Ti-based amorphous alloys have great potential for the application in, for example, medical devices, bio-medical implants and medical materials, owing to the excellent properties of amorphous alloys, such as corrosion resistance, wear resistance and so on, and their related research presents great promise in both scientific and practical applications.

The medical drill according to the present invention can be shaped in a pillar body by a turning process, and a spiral structure can be formed in a portion of the pillar body. The medical drill according to the present invention may be manufactured by preparing an amorphous alloy rod through rapid cooling, forming a spiral structure in a portion of the amorphous alloy rod by heating (not higher than crystallization temperature (Tx)) and then a stretching and twisting process, and finally cooling it to obtain the medical drill according to the present invention.

Preferably, the medical drill according to the present invention is shaped in a pillar body, and a thread is formed in a part of the pillar body. The medical drill according to the present invention may be manufactured by preparing an amorphous alloy rod through rapid cooling, and forming a spiral structure in a portion of the amorphous alloy rod by a sculpturing process to thereby obtain the medical drill according to the present invention.

In the process for manufacturing the medical drill according to the present invention, the processing method of the amorphous alloy rod is not limited to a stretching and twisting process and a sculpturing process, and may use other processing methods of metal materials as long as the arrangement of metal atoms in the amorphous alloy would not be damaged in the processing way (that is, the processing temperature cannot exceed the crystallization temperature (Tx)).

According to the medical drill of the present invention, the Zr-based amorphous alloy preferably contains zirconium in 45 at % or more, aluminum in 5-10 at %, copper in 15-20 at % and nickel in 5-15 at %.

According to the medical drill of the present invention, the Zr-based amorphous alloy preferably further contains silicon, boron, yttrium, palladium or tantalum in 1 at % or more.

According to the medical drill of the present invention, the Zr-based amorphous alloy preferably is represented by the following formula 1, $$Zr_a Al_b Cu_c Ni_d Si_e, \quad \text{[formula 1]}$$

in which, $45=<a=<75$, $5=<b=<10$, $15=<c=<20$, $5=<d=<15$, $1=<e=<10$.

According to the medical drill of the present invention, the Zr-based amorphous alloy preferably further contains Si and other elements so as to enhance the packing density of atoms in the amorphous alloy, improve the thermal stability and mechanical properties of the amorphous alloy, and maintain longer incubation time during isothermal annealing in the supercooled liquid region. In addition, it is confirmed that the addition of an Si element can enhance the thermal stability of the Zr-based amorphous alloy to be 2-3 times higher compared to the addition of a boron element.

According to the medical drill of the present invention, the formula 1 preferably is $Zr_{61}Al_{7.5}Cu_{17.5}Ni_{10}Si_4$.

According to the medical drill of the present invention, the Zr-based amorphous alloy preferably is represented by the following formula 2, $$Zr_aAl_bCu_cNi_dB_e,\qquad\text{[formula 2]}$$

in which, $45=<a=<75$, $5=<b=<10$, $15=<c=<20$, $5=<d=<15$, $1=<e=<10$.

According to the medical drill of the present invention, the formula 2 preferably is $Zr_{61}Al_{7.5}Cu_{17.5}Ni_{10}B_2$.

In the present invention, the Zr-based amorphous alloy preferably further contains boron and other elements in addition to Zr metal so as to improve the thermal stability of the Zr-based amorphous alloy and to maintain longer incubation time during isothermal annealing in the supercooled liquid region.

According to the medical drill of the present invention, the Zr-based amorphous alloy preferably is represented by the following formula 3, $$Zr_aAl_bCu_cNi_dB_e,\qquad\text{[formula 3]}$$

in which, $45=<a=<75$, $5=<b=<10$, $15=<c=<30$, $5=<d=<15$, $1=<e=<15$.

According to the medical drill of the present invention, the formula 3 preferably is $Zr_{53}Cu_{30-x}Ni_9Al_8Ta_x$, in which $0.1=<x=<10$.

In the present invention, the Zr-based amorphous alloy further contains tantalum and other elements in addition to Zr metal. Through tests, it can be confirmed that the addition of tantalum can increase plastic deformation of the amorphous alloy rod and thus makes the subsequent process more convenient to be performed.

According to the medical drill of the present invention, the Zr-based amorphous alloy preferably is represented by the following formula 4, $$Zr_aAl_bCu_cPd_dNb_e,\qquad\text{[formula 4]}$$

in which, $45=<a=<75$, $5=<b=<10$, $15=<c=<30$, $0=<d=<9$, $0=<e=<9$.

According to the medical drill of the present invention, the formula 4 preferably is $Zr_{53}Al_8Cu_{30}Pd_xNb_y$, in which x=4.5, y=4.5. The nickel-free Zr-based amorphous alloy can have higher ductility and toughness.

The present invention further provides a medical drill made of an amorphous alloy, in which the amorphous alloy is a Ti-based amorphous alloy which contains titanium in 40 at % or more, and the Ti-based amorphous alloy has a tensile strength (maximum tensile strength) of 1600-2600 MPa and a Vickers hardness of 600-800. For example, the Ti-based amorphous alloy can be 2148 MPa in tensile strength (maximum tensile strength) and 709 in Vickers hardness.

The medical drill of the present invention may be used as a bone drill or a dental drill. Through tests under practical operation, it can be confirmed that the medical drill made of the amorphous alloy according to the present invention has excellent properties of good fracture resistance, enhanced corrosion resistance, high wear resistance, improved toughness and high hardness compared to conventional medical drills made of crystalline alloys. That is, the conventional art cannot achieve the above-mentioned excellent properties. In addition, the Ti-based amorphous alloy has reduced weight due to titanium being lighter in weight, and has an elastic limit of 6% or more.

In the present invention, the amorphous alloys are applied in medical bone drills and exhibit better properties compared to the alloy materials used in conventional drills. The drill made of the amorphous material according to the present invention has excellent properties equal to surgical knifes, such as good toughness, high hardness and enhanced fracture resistance, and thus can meet the requirements for medical use.

The amorphous alloys of the present invention include Ti-based amorphous alloys and have higher glass transition temperature and activation energy. In addition, silicon, boron, yttrium, palladium or tantalum may be added into the Ti-based amorphous alloys to enhance the thermal stability and mechanical properties of the amorphous alloys (or to inhibit crystallized nucleation of supercooled metallic liquid).

So far, little research focuses on the application of amorphous materials in clinical medicine. The Zr-based or Ti-based amorphous alloys have great potential for the application in, for example, medical devices, bio-medical implants and medical materials, owing to the excellent properties of amorphous alloys, such as corrosion resistance, wear resistance and so on, and their related research presents great promise in both scientific and practical applications.

The medical drill according to the present invention can be shaped in a pillar body, and a spiral structure can be formed in a portion of the pillar body. The medical drill according to the present invention may be manufactured by preparing an amorphous alloy rod through rapid cooling, forming a spiral structure in a portion of the amorphous alloy rod by heating (not higher than crystallization temperature (Tx)) and then a stretching and twisting process, and finally cooling it to obtain the medical drill according to the present invention.

Preferably, the medical drill according to the present invention is shaped in a pillar body, and a thread is formed in a part of the pillar body. The medical drill according to the present invention may be manufactured by preparing an amorphous alloy rod through rapid cooling, and forming a spiral structure in a portion of the amorphous alloy rod by a sculpturing process to thereby obtain the medical drill according to the present invention.

The process for manufacturing the medical drill according to the present invention, the processing method of the amorphous alloy rod is not limited to a stretching and twisting process and a sculpturing process, and may use other processing methods of metal materials as long as the arrangement of metal atoms in the amorphous alloy would not be damaged in the processing way (that is, the processing temperature cannot exceed the crystallization temperature (Tx)).

According to the medical drill of the present invention, the Ti-based amorphous alloy preferably contains titanium in 40 at % or more, copper in 30-40 at %, palladium in 10-20 at % and zirconium in 5-15 at %.

According to the medical drill of the present invention, the Ti-based amorphous alloy preferably further contains Si in 1 wt % or more. In the medical drill of the present invention, silicon and other elements preferably can be added therein so as to enhance the packing density of atoms in the amorphous alloy, improve the thermal stability and mechanical properties of the amorphous alloy, and maintain longer incubation time during isothermal annealing in the supercooled liquid region. In addition, it is confirmed that the addition of an Si element can enhance the thermal stability of the Ti-based amorphous alloy to be 2-3 times higher compared to the addition of boron element.

According to the medical drill of the present invention, the Ti-based amorphous alloy preferably is represented by the following formula 5,

in which, 40=<a=<75, 30=<b=<40, 10=<c=<20, 5=<d=<15, 0.05=<e=<2.

DETAILED DESCRIPTION OF THE PREFERRED EMBODIMENT

Hereafter, examples will be provided to illustrate the embodiments of the present invention. Those skilled in the art can easily understand the advantages and effects of the invention from the disclosure of the present invention. The following examples are intended for illustrating the embodiments of the subject invention, but not for excluding other embodiments. Those skilled in the art can omit, modify, reduce or vary components without departing from the spirit of the invention.

EXAMPLE 1

Medical Drill of Zr-Based Amorphous Alloy

An amorphous alloy rod (8 mmφ×70 mm L) is manufactured by using $Zr_{61}Al_{7.5}Cu_{17.5}Ni_{10}Si_4$ as the material and performing suction casting and rapid cooling.

Figure 1:
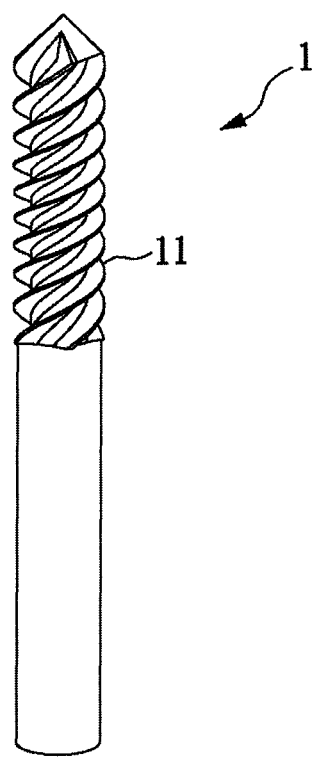
FIG. 1 is a schematic diagram of a conventional medical drill.
Figure 2:
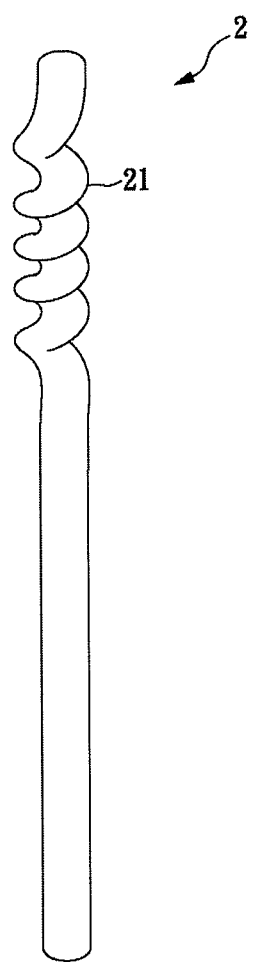
FIG. 2 is a schematic diagram of a medical drill according to Example 1 of the present invention.

Subsequently, the amorphous alloy rod is processed at normal temperature, and a stretching and twisting process is performed in a low-temperature water recycling system which can ensure the work temperature is not higher than the crystallization temperature (Tx) to form a spiral structure in a certain portion of the amorphous alloy rod and thereby to obtain the medical drill of the present example, as shown in FIG. 2.

As shown in FIG. 2, the medical drill 2 according to the present example has a pillar body of which a certain portion 21 is structured in a spiral shape. Additionally, the medical drill 2 according to the present example is made of Zr-based amorphous alloy containing 45% or more of Zr metal.

In the present example, the Zr-based amorphous alloy further contains Si and other elements in addition to Zr metal so as to enhance the packing density of atoms in the amorphous alloy, improve the thermal stability and mechanical properties of the amorphous alloy, and maintain longer incubation time during isothermal annealing in the supercooled liquid region. In addition, it is confirmed that the addition of an Si element can enhance the thermal stability of the Zr-based amorphous alloy to be 2-3 times higher compared to the addition of a boron element.

The tensile strength, Vickers hardness and specific gravity of the medical drill made of the Zr-based amorphous alloy according to the present example is measured as 1600-1800 MPa, 550-650 and 5.9-6.7 kg/L, respectively. The above-mentioned excellent properties cannot be found in general crystalline metal.

The medical drill according to the present example can be used as a bone drill or a dental drill. Through tests under practical operation, it can be confirmed that the medical drill made of the amorphous alloy according to the present example has excellent properties of good fracture resistance, enhanced corrosion resistance, high wear resistance, improved toughness and high hardness compared to conventional medical drills made of crystalline alloys. That is, the conventional art cannot achieve the above-mentioned excellent properties.

EXAMPLE 2

Medical Drill of Zr-Based Amorphous Alloy

An amorphous alloy rod (10 mmφ×60 mm L) is manufactured by using $Zr_{61}Al_{7.5}Cu_{17.5}Ni_{10}B_2$ as the material and performing suction casting and rapid cooling.

Subsequently, the amorphous alloy rod is processed at normal temperature, and a stretching and twisting process is performed in a low-temperature water recycling system which can ensure the work temperature is not higher than the crystallization temperature (Tx) to form a spiral structure in a certain portion of the amorphous alloy rod and thereby to obtain the medical drill of the present example.

In the present example, the Zr-based amorphous alloy further contains boron and other elements in addition to Zr metal so as to improve the thermal stability and mechanical properties of the Zr-based amorphous alloy, and maintain longer incubation time during isothermal annealing in the supercooled liquid region.

EXAMPLE 3

Medical Drill of Zr-Based Amorphous Alloy

The medical drill made of Zr-based amorphous alloy according to the present example is manufactured by the same process as that illustrated in Example 1, except that the present example uses $Zr_{53}Cu_{30-x}Ni_9Al_8Ta_x$ as material and the size of the amorphous alloy rod prepared in the present example is 2 mmφ×30 mm L.

In the present example, the Zr-based amorphous alloy further contains tantalum and other elements in addition to Zr metal. Through tests, it can be confirmed that the addition of tantalum can increase plastic deformation of the amorphous alloy rod and thus makes the subsequent process more convenient to be performed.

EXAMPLE 4

Medical Drill of Zr-Based Amorphous Alloy

The medical drill made of Zr-based amorphous alloy according to the present example is manufactured by the same process as that illustrated in Example 1, except that the present example uses $Zr_{63.8}Ni_{16.2}Cu_{15}Al_5$ as material.

In the present example, the Zr-based amorphous alloy contains Zr metal as a major component and nickel, copper and aluminum, but does not contain metalloid elements, i.e. silicon and boron.

EXAMPLE 5

Medical Drill of Zr-Based Amorphous Alloy

The medical drill made of Zr-based amorphous alloy according to the present example is manufactured by the same process as that illustrated in Example 1, except that the present example uses $Zr_{53}Al_8Cu_{30}Pd_xNb_y$ (x=4.5, y=4.5) as material.

In the present example, the medical drill is made of nickel-free Zr-based amorphous alloy and has higher ductility and toughness.

EXAMPLE 6

Medical Drill of Ti-Based Amorphous Alloy

An amorphous alloy rod (5 mm$\phi$×50 mm L) is manufactured by using $Ti_aCu_bPd_cZr_dSi_e$ (40=<a=<75, 30=<b=<40, 10=<c=<20, 5=<d=<15, 0.05=<e=<2) as the material and performing suction casting and rapid cooling.

Subsequently, the amorphous alloy rod is processed at normal temperature, and a stretching and twisting process is performed in a low-temperature water recycling system which can ensure the work temperature is not higher than the crystallization temperature (Tx) to form a spiral structure in a certain portion of the amorphous alloy rod and thereby to obtain the medical drill of the present example. Regarding the medical drill made of the Ti-based amorphous alloy according to the present example, the Ti-based amorphous alloy is measured as 2148 MPa in tensile strength (maximum tensile strength) and 709 in Vickers hardness.

The medical drill according to the present example has reduced weight due to titanium weighing less weight, and has an elastic limit of 6% or more.

EXAMPLE 7

Medical Drill of Zr-Based Amorphous Alloy

An amorphous alloy rod (10 mm$\phi$×60 mm L) is manufactured by using $Zr_{61}Al_{7.5}Cu_{17.5}Ni_{10}B_2$ as the material and performing suction casting and rapid cooling.

Figure 3:
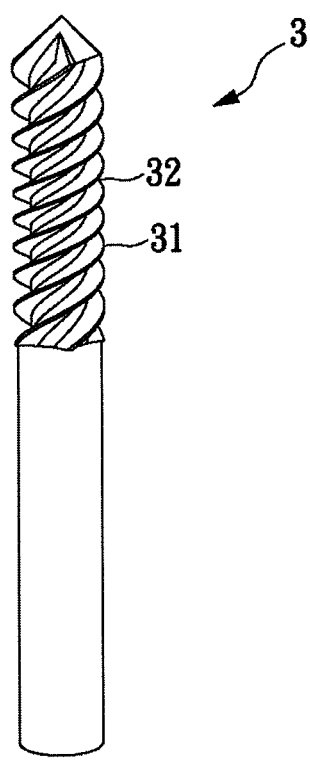
FIG. 3 is a schematic diagram of a medical drill according to Example 7 of the present invention.

Subsequently, the amorphous alloy rod is processed by a sculpturing process to form threads in a certain portion of the amorphous alloy rod and thereby to obtain the medical drill of the present example, as shown in FIG. 3.

As shown in FIG. 3, the medical drill 3 according to the present example has a pillar body, and threads 32 are formed in a certain portion 31 of the pillar body. Additionally, the medical drill 3 according to the present example is made of Zr-based amorphous alloy containing 45 at % or more of Zr metal.

In the present example, the amorphous alloy rod is processed by a sculpturing process rather than a stretching and twisting process. In the present invention, the amorphous alloy rod may be processed in other processing ways in addition to a stretching and twisting process and a sculpturing process, as long as the arrangement of metal atoms in the amorphous alloy would not be damaged in the processing way (that is, the processing temperature cannot exceed the crystallization temperature (Tx)).

In the present invention, the amorphous alloys are applied in medical bone drills and exhibit better properties compared to the alloy materials used in conventional drills. The drill made of the amorphous material according to the present invention has excellent properties equal to surgical knives, such as good toughness, high hardness and enhanced fracture resistance, and thus can meet the requirements for medical use.

The amorphous alloys of the present invention include Zr-based amorphous alloys and Ti-based amorphous alloys and have higher glass transition temperature and activation energy. In addition, silicon, boron, yttrium, palladium or tantalum may be added into the amorphous alloys to enhance the thermal stability and mechanical properties of the amorphous alloys (or to inhibit crystallized nucleation of supercooled metallic liquid).

So far, little research focuses on the application of amorphous materials in clinical medicine. The Zr-based or Ti-based amorphous alloys have great potential for the application in, for example, medical devices, bio-medical implants and medical materials, owing to the excellent properties of amorphous alloys, such as corrosion resistance, wear resistance and so on, and their related research presents great promise in both scientific and practical applications.

The above examples are intended for illustrating the embodiments of the subject invention and the technical features thereof, but not for restricting the scope of protection of the subject invention. The scope of the subject invention is based on the claims as appended.

What is claimed is:

1. A medical drill made of an amorphous alloy, wherein the amorphous alloy is a Zr-based amorphous alloy which comprises zirconium metal in 45 at % or more, and the medical drill has a tensile strength of 1500-2500 MPa and a Vickers hardness of 400-750;
   wherein the Zr-based amorphous alloy comprises zirconium in 45 at % or more, aluminum in 5-10 at %, copper in 15-20 at % and nickel in 5-15 at %, and further comprises silicon, boron, yttrium, palladium or tantalum in 1 at % or more;
   wherein the Zr-based amorphous alloy is represented by the following formula of $Zr_{61}Al_{7.5}Cu_{17.5}Ni_{10}B_2$.

2. The medical drill as claimed in claim 1, wherein the medical drill is shaped in a pillar body, and a spiral structure is formed in a portion of the pillar body.

3. The medical drill as claimed in claim 1, wherein the medical drill is shaped in a pillar body, and a thread is formed in a portion of the pillar body.

4. The medical drill as claimed in claim 1, wherein the medical drill is manufactured by:
   a) preparing an amorphous alloy rod through rapid cooling;
   b) forming a spiral structure in a portion of the amorphous alloy rod by heating; and
   c) a stretching and twisting process;
   wherein a temperature of step (b) is not higher than a crystallization temperature (Tx) of the amorphous alloy.

5. A medical drill made of an amorphous alloy, wherein the amorphous alloy is a Zr-based amorphous alloy which comprises zirconium metal in 45 at % or more, and the medical drill has a tensile strength of 1500-2500 MPa and a Vickers hardness of 400-750;
   wherein the Zr-based amorphous alloy comprises zirconium in 45 at % or more, aluminum in 5-10 at %, copper in 15-20 at % and nickel in 5-15 at %, and further comprises silicon, boron, yttrium, palladium or tantalum in 1 at % or more;
   wherein the Zr-based amorphous alloy is represented by the following formula of $Zr_{53}Cu_{30-x}Ni_9Al_8Ta_x$ therewith 0.1=<x=<10.

6. The medical drill as claimed in claim 5, wherein the medical drill is manufactured by:
   a) preparing an amorphous alloy rod through rapid cooling;
   b) forming a spiral structure in a portion of the amorphous alloy rod by heating; and
   c) a stretching and twisting process;
   wherein a temperature of step (b) is not higher than a crystallization temperature (Tx) of the amorphous alloy.

7. A medical drill made of an amorphous alloy, wherein the amorphous alloy is a Zr-based amorphous alloy which comprises zirconium metal in 45 at % or more, and the medical drill has a tensile strength of 1500-2500 MPa and a Vickers hardness of 400-750;
   wherein the Zr-based amorphous alloy comprises zirconium in 45 at % or more, aluminum in 5-10 at %, copper in 15-20 at % and nickel in 5-15 at %, and further comprises silicon, boron, yttrium, palladium or tantalum in 1 at % or more;
   wherein the Zr-based amorphous alloy is represented by the following formula of $Zr_{53}Al_8Cu_{30}Pd_xNb_y$, therewith x=4.5 and y=4.5.

8. The medical drill as claimed in claim 7, wherein the medical drill is manufactured by:
   a) preparing an amorphous alloy rod through rapid cooling;
   b) forming a spiral structure in a portion of the amorphous alloy rod by heating; and
   c) a stretching and twisting process;
   wherein a temperature of step (b) is not higher than a crystallization temperature (Tx) of the amorphous alloy.

* * * * *